United States Patent [19]

Law et al.

[11] Patent Number: 5,411,870
[45] Date of Patent: * May 2, 1995

[54] PROCESS AND APPARATUS FOR DIRECT DETERMINATION OF LOW DENSITY LIPOPROTEIN

[75] Inventors: Wai T. Law, Sewell; Gerhard Ertingshausen, Princeton, both of N.J.

[73] Assignee: ActiMed Laboratories, Inc., Burlington, N.J.

[*] Notice: The portion of the term of this patent subsequent to Feb. 15, 2011 has been disclaimed.

[21] Appl. No.: 987,962

[22] Filed: Dec. 11, 1992

Related U.S. Application Data

[63] Continuation-in-part of Ser. No. 806,183, Dec. 13, 1991, Pat. No. 5,286,626.

[51] Int. Cl.⁶ .................... C12Q 1/60; C12Q 1/00; G01N 33/92; G01N 31/00
[52] U.S. Cl. .......................... 435/11; 435/4; 435/7.9; 435/7.1; 435/25; 435/23; 435/19; 436/71; 436/13; 436/181
[58] Field of Search .............. 435/11, 7, 4, 19, 13, 435/7.9, 7.1, 25, 23; 436/181, 17, 825, 71, 19, 13

[56] References Cited

U.S. PATENT DOCUMENTS

| | | | |
|---|---|---|---|
| 3,814,255 | 6/1974 | Smernoff | 210/656 |
| 4,126,416 | 11/1978 | Sears | 436/71 |
| 4,210,557 | 7/1980 | Handschuh | 436/17 |
| 4,226,713 | 10/1980 | Goldberg | 435/11 |
| 4,366,244 | 12/1982 | Pascal | 435/11 |
| 4,474,887 | 10/1984 | Maier et al. | 435/71 |
| 4,486,531 | 12/1984 | Ziegenhorn et al. | 435/19 |
| 4,579,825 | 4/1986 | Siedel et al. | 436/71 |
| 4,647,280 | 3/1987 | Maaskant et al. | 604/5 |
| 4,746,605 | 5/1988 | Kerscher et al. | 435/7 |
| 5,168,067 | 12/1992 | Miller et al. | 436/181 |

FOREIGN PATENT DOCUMENTS

| | | |
|---|---|---|
| 0013814 | 8/1980 | European Pat. Off. . |
| 0428980A1 | 5/1991 | European Pat. Off. . |
| 0035211 | 9/1981 | Germany . |
| 0174478 | 11/1988 | Germany . |

OTHER PUBLICATIONS

Random House Dictionary, p. 1391 (1967).

*Primary Examiner*—Michael G. Wityshyn
*Assistant Examiner*—Louise N. Leary
*Attorney, Agent, or Firm*—Iver P. Cooper

[57] ABSTRACT

Low density lipoproteins are directly determined in fluid samples by selectively precipitating low density lipoproteins from the sample by forming clusters, selectively consuming the high density and very low density lipoproteins, and resolubilizing the low density lipoproteins for direct determination thereof. The clusters are formed by treating the fluid sample with a mixture of a polyanionic compound, a divalent metal, and a nucleating agent. The clusters are redissolved and assayed for low density lipoproteins.

9 Claims, 1 Drawing Sheet

FIG.1.
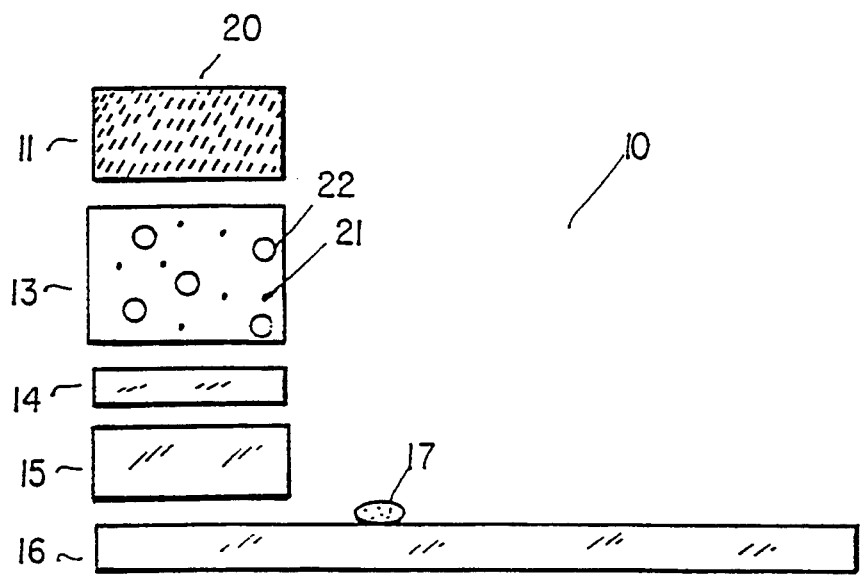
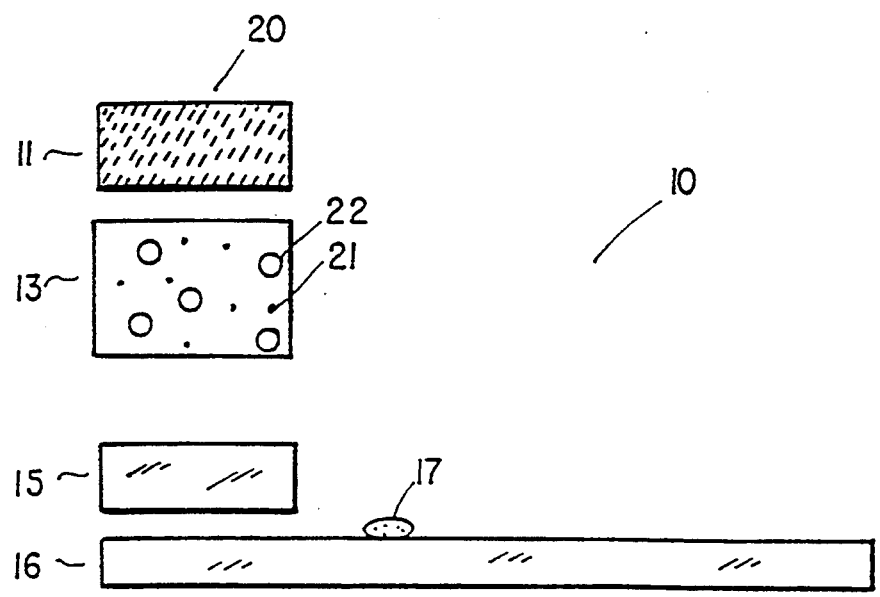
FIG.2.

PROCESS AND APPARATUS FOR DIRECT DETERMINATION OF LOW DENSITY LIPOPROTEIN

This application is a continuation-in-part of Ser. No. 07/806,183, filed Dec. 13, 1991, now patented as U.S. Pat. No. 5,286,626, issued Feb. 15, 1994.

FIELD OF THE INVENTION

The present invention relates to a process for the direct determination of low density lipoprotein in body fluids. More specifically, the present invention relates to a process and apparatus for determination of low density lipoprotein by selectively precipitating low density lipoprotein from a sample, providing enzymes which selectively consume the high density lipoprotein, and then resolubilizing the low density fraction and determining this fraction enzymatically.

BACKGROUND OF THE INVENTION

Lipoproteins are complex particles consisting of protein and lipid which are found in the circulatory system. One of the functions of lipoproteins is to carry water-insoluble substances such as cholesterol and cholesterol esters for eventual cellular use. While all cells require cholesterol for growth, excess accumulation of cholesterol by cells is known to lead to certain diseases, including atherosclerosis.

It is known that the amount of total serum cholesterol can be correlated with the incidence of atherosclerosis. However, there are a variety of classes of lipoproteins in serum which can be classified by their density. These classes include very low density lipoproteins (VLDL), low density lipoproteins (LDL) and high density lipoproteins (HDL). All of these classes of lipoproteins contain varying amounts of cholesterol, and a total serum cholesterol determination is a complex average of the amount that each lipoprotein-class contributes to the total lipoprotein population of the serum.

It has long been suspected that some lipoprotein classes are more closely associated than other lipoprotein classes with the progression of heart disease, including atherosclerosis. In fact more recent studies have implicated LDL as the class of lipoproteins responsible for the accumulation of cholesterol in cells, whereas HDL has been shown to be important in the removal of excess cholesterol from cells. Additionally the correlation of atherosclerosis and the levels of LDL cholesterol is much higher than a similar correlation between atherosclerosis and total serum cholesterol levels. Conversely, there appears to be a negative correlation between atherosclerosis and HDL cholesterol levels.

Despite the desirability of differentiating LDL cholesterol levels in blood plasma from those of other soluble cholesterols, a technique suitable for use in clinical laboratories has not heretofore existed. One method which has been suggested relies upon the interaction of heparin in the presence of calcium to precipitate both LDL and VLDL, cf. Bursterin et al., *Adv. Lipid. Res.* 11:67 (1973). To separate the LDL and VLDL fractions, ultracentrifugation techniques, which are time consuming and expensive, may be used. Ultracentrifugation, to separate the lipoproteins solely on the basis of their density, requires special equipment and long processing time. Electrophoretic separation also requires special equipment and long processing times.

A variety of precipitation methods have been used which depend upon the use of polyanions and divalent cations, Okabe, Xth Int. Cong. of Clin. Chem., Mexico (1978); Genzyme Diagnostic, Cambridge, Mass., LDL cholesterol precipitation reagent package insert. Other precipitation methods use polymers, as shown in U.S. Pat. No. 4,474,898 and U.S. Pat. No. 4,647,280; or lectin, as disclosed in U.S. Pat. No. 4,126,416. Kerscher et al., in U.S. Pat. No. 4,746,605, teach that VLDL and HDL can be precipitated by HDL antibodies with polyanions and divalent cations. However, the amount of antibodies required with this method is too expensive for routine use.

Other methods for determining the amount of lipoprotein fractions in samples are known, but these methods are not suitable for use in a dry-chemistry device which can be used for simple and rapid determination of lipoproteins. For example, Pascal, in U.S. Pat. No. 4,366,244, discloses that lipoprotein fractions can be separated by using a lectin to separate the LDL and VLDL fractions, and then measuring the amount of cholesterol in the precipitate and in the remaining solution. This method requires centrifugation of the precipitate, and measurement of both the precipitate and the remaining solution. Ziegenhorn et al., in U.S. Pat. No. 4,486,531, disclose a turbidimetric process for detection of beta-lipoproteins (LDL) in body fluids by precipitation with polyanions and divalent cations. The LDL then can be detected directly by a turbidimetric determination.

When LDL is precipitated with polyanions such as dextran sulfate and divalent cations such as magnesium, the precipitate redissolves if one tries to selectively convert the cholesterol in the supernatant by an enzymatic assay which requires the presence of surfactants. Moreover, cholesterol esterase and cholesterol oxidase present in the system hydrolyze the LDL.

Another method for determining LDL is calculation by the Friedewald Formula, as disclosed in Friedewald et al., *Clin. Chem.* 18: 499–502 (1972). In this method, LDL is estimated by the total cholesterol, HDL, and triglyceride contents of the sample. This method requires multiple assays, and is not accurate for samples containing high levels of triglycerides.

Consequently, there is a need for a simple procedure or device for the determination of LDL lipoprotein accurately.

SUMMARY OF THE INVENTION

It is an object of the present invention to overcome the aforementioned deficiencies in the background art. The present invention provides a simple method and apparatus for the determination of LDL. An important feature of this invention is the use of nucleating particles to facilitate precipitation of LDL in stable form.

According to the present invention, a precipitating reagent for LDL is added to a fluid sample. The LDL present in the sample rapidly precipitates, and enzymes are added to react with HDL and VLDL in the sample. The LDL is then redissolved, and the LDL is detected by any conventional means.

LDL precipitate normally dissolves quickly in the presence of surfactants such as sodium cholate, and cholesterol esterase usually rapidly hydrolyzes any cholesterol esters in lipoproteins in the presence of suitable surfactants. However, the presence of sufficient small particles to provide nucleating agents for clusters of LDL stabilizes the clusters against the effect both of surfactants and of cholesterol esterase.

Alternatively, the VLDL can be precipitated first, and then the LDL is precipitated with the specific precipitating reagents and nucleating particles of the present invention. Enzymes are added to react with HDL in the sample, and the LDL is redissolved and detected according to conventional detection means for LDL. Enzymatic means for detecting LDL are preferred.

The nucleating particles preferably range in size from about 0.1 to about 100 microns, and may be either mixed with the polyanionic compound or the polyanionic compound may be immobilized thereon. The preferred particles are porous iron oxide.

The advantage of the method of the present invention is that LDL can be effectively separated from other components of whole blood to provide a reliable, quantitative assay of LDL. Additionally, this method proceeds very quickly (usually in less than 120 seconds), so it is particularly well suited for use in disposable assay devices as described in this specification.

BRIEF DESCRIPTION OF THE DRAWINGS

FIG. 1 is a side view of a direct LDL measurement device according to the present invention.

FIG. 2 is a side view of another direct LDL measurement device according to the present invention.

DETAILED DESCRIPTION OF THE INVENTION

According to the present invention, a fluid sample, such as whole blood, is treated with a precipitating reagent to form clusters of LDL. This precipitating reagent preferably comprises a mixture of large polyanions and divalent cations, and the precipitation reaction is mediated by nucleating particles. The clusters of LDL so formed are surprisingly stable in the presence of cholesterol enzymes. Cholesterol enzymes, such as cholesterol oxidase and cholesterol esterase, are then added to the sample. At this point the HDL and VLDL lipoproteins in the liquid phase are consumed, while the solid phase LDL clusters remain intact. The LDL is then redissolved by a redissolution agent, and is then analyzed by any conventional means. One convenient method of analyzing the LDL is by enzymatic analysis to form hydrogen peroxide, which is then assayed colorimetrically.

The greater the specificity of the precipitating agent for LDL, the more useful it is in the present invention. However, some precipitation of HDL and/or VLDL may be tolerable, depending on the diagnostic context. Preferably, the lipoprotein precipitates are at least 90% LDL.

Alternatively, instead of precipitating LDL and then removing the HDL and VLDL, the VLDL can be selectively precipitated first. After the VLDL has been precipitated from the sample, clusters of LDL are then formed by adding a polyanionic compound, a salt of a divalent metal and a nucleating agent to the sample. Appropriate enzymes are then added to consume HDL, and the LDL clusters are treated with a redissolution agent to resolubilize the LDL for determination by conventional means.

The polyanions that can be used for forming the LDL clusters can be any polyanions which precipitate lipoproteins which do not interfere with subsequent assays for LDL. Among the polyanions that can be used are dextran sulfate, heparin, phosphotungstic acid, and polyvinyl sulfate. The dextran sulfate can be high molecular (i.e., molecular weight of from $5 \times 10^4$ to $2 \times 10^6$) or short-chained (molecular weight of from 5000 to 50,000). The preferred concentration ranges of the polyanions in the reaction mixture are from about 0.1 to about 8 grams/liter in the case of high molecular weight dextran sulfate, from about 1 to about 15 grams/liter in the case of short-chained dextran sulfate and heparin, from about 0.2 to about 5 grams/liter in the case of polyvinyl sulfate, and from about 0.3 to about 6 grams/liter in the case of phosphotungstic acid.

The polyvinyl sulfate is a polymer derived from polyvinyl alcohol, of which polymer at least 20% of the vinyl alcohol groups are sulfated. The molecular weight of the polyvinyl alcohol is not critical as long as it can be crosslinked. This is generally the case at a molecular weight of about 5000 or higher. Very favorable results can be obtained at molecular weights in the range of 10,000 to 150,000 or more. For best results, at least 50% of the vinyl groups are sulfated. Optimum results are obtained wherein at least about 65% of the vinyl alcohol groups are sulfated. Sulfation of the polyvinyl alcohol is preferably carried out using a reaction product of sulfur trioxide or cholorsulfonic acid and a Lewis base. Particularly suitable is the addition product of pyridine to sulfur trioxide. The sulfation reaction is preferably carried out in dimethyl formamide or formamide at a temperature of between 60° and 110° C. The polyvinyl alcohol may be crosslinked before or after sulfation, and the crosslinking may be effected either chemically or physically.

The divalent cations that can be used in the system of the present invention include the II-A and II-B cations, particularly calcium, magnesium and manganese. As with polyvalent anions, the divalent cations may be of any species which has the desired precipitating effect and which does not interfere with the subsequent LDL determinations. These cations can be added in the form of a soluble salt such as a chloride salt. The concentration of the divalent metal ions to be added is preferably from about 10 to about 250 mMole/liter in the reaction mixture. A conventional buffer can be used to buffer in a pH range of from about 6.5 to about 8.5, such as MES (morpholino ethane sulfonic acid), triethanolamine, MOPS (morpholino propane sulfonic acid) or Tris buffer.

The invention is not limited to the use of any particular precipitating agent.

Once the LDL fraction has been separated from the other components in the sample, conventional methods of analysis can be used for the LDL determination. The LDL determination can, for example, take place by saponification with alcoholic potassium hydroxide solution and chemical determination according to Liebermann-Burchard. However, it is preferred to use an enzymetic determination using cholesterol oxidase (CO) and a cholesterol ester-splitting enzyme or enzyme system, such as cholesterol esterase (CE). In the case of the use of cholesterol oxidase, the determinations can be based upon the amount of oxygen consumed, the amount of cholest-4-one-3-one formed, or the amount of hydrogen peroxide formed using conventional methods for this purpose. Since the determination of bound cholesterol is well known, there is no need to describe it it detail. The invention is not limited to any method of determining a precipitated LDL.

The particles that can be used as nucleating agents for forming the LDL clusters can be any nucleating particles that do not interfere with the subsequent assay for LDL. For example, iron oxide, chromium dioxide, stainless steel, silicon dioxide, glass, methyl methacrylate particles, and the like can all be used. These nucleating agents must be insoluble in the liquids used in the assay, i.e., generally insoluble in water. The particle may be organic or inorganic, and, if inorganic, may be amorphous or crystalline. The inorganic salts may be, but are not limited to, metal salts, such as salts of iron or chromium. Among inorganic salts, metal or otherwise, oxide (including dioxide) salts are preferred, as they are unlikely to interfere with an oxidative reaction. The particle size is preferably between about 0.5 and 200 microns, more preferably 1-10 microns. However, to obtain a precipitate of large agglomerates (e.g., larger than about 100 microns) in less than 60 seconds, which is particularly useful with the devices disclosed herein, porous iron oxide with an average diameter of from about 1 to about 10 microns (Reference Diagnostics, Arlington, Mass.), is most preferred.

The nucleating agents can be added in with a mixture of the polyanionic compound and the divalent metal. Alternatively, the nucleating agents can be coated with the polyanionic compound or various compounds and added along with the divalent metal to the fluid sample.

Preferably, the nucleating agent precipitates more than 50%, more preferably, at least 75%, still more preferably at least 95% of the LDL. Preferably, substantial precipitation occurs in less than 120 seconds, more preferably less than 60 seconds, still more preferably less than 30 seconds. It is desirable that a good solid pellet be formed and that the pellet be readily redissolved by the redissolving agent. Preferably, the nucleating agent stabilizes the precipitate so that less than 20%, more preferably less than 10%, is redissolved by cholesterol esterase and/or cholesterol oxidase.

The redissolution agent, for redissolving the LDL that was found to be most effective was a mixture of EDTA and sodium chloride, however, the invention is not limited to this agent. Other chaotropic agents and/or surfactants known in the art may be used. When a combination of EDTA and sodium chloride is used, a solution of 2.5-6.5% sodium chloride and 0.05-0.10% EDTA is especially preferred. Other redissolution agents, such as from about 75-100 units protease per test and from 50 to 200 mM magnesium chloride per test can also be used. The redissolution agents change the ionic strength of the sample, breaking up the lipoprotein clusters in less than thirty seconds. The redissolution agent may be provided in a liquid or solid (but solubilizable) phase.

The process of the present invention is particularly well suited for use in devices colorimetrically which register the amount or presence of LDL in a sample. Because the reaction of the present invention proceeds quite rapidly, generally within about 120 seconds, a reading can be obtained within a short time, so that the test can be performed in, for example, a physician's office or a health clinic. The following exemplify two types of devices which can be used with the process of the present invention. Of course, these examples are for illustrative purposes only, and not for limitation.

Referring to FIG. 1, one embodiment of a device according to the present invention is shown at 10. A fluid sample is introduced to the device at a sample initiation area 20, and red blood cells are trapped in layer 11. Plasma then enters an LDL precipitation zone, layer 13. A particle enhanced LDL precipitation reagent 21 in zone 13 causes the LDL to precipitate in large clusters 22 in less than 60 seconds. The enzymes cholesterol esterase (CE) and cholesterol oxidase (CO), together with the surfactants deposited in zone 13, react with the HDL and VLDL to produce hydrogen peroxide. Surprisingly, the particle enhanced LDL precipitate 22 does not dissolve and does not react with the cholesterol enzymes, so that only the HDL and the VLDL react with the cholesterol enzymes, and the hydrogen peroxide generated thereby is consumed by endogenous catalase in less than ten minutes.

Zone 14 is a thin sucrose coating and is designed to dissolve in less than ten minutes. An alternative dissolvable coating may also be used. An LDL redissolution zone, zone 15, contains dried hydroxylamine (HA), or an alternative catalase inhibitor, and LDL redissolution agents. When zone 14 is dissolved, both the hydroxylamine and the LDL redissolution agents are mixed with the contents of the LDL precipitating zone 13, where the catalase is inhibited by hydroxylamine and the LDL clusters are then dissolved by the action of the LDL redissolution agents. The re-dissolved LDL then reacts with cholesterol oxidase and cholesterol esterase, or other agents which catalyze hydrogen peroxide-generating reactions when LDL is available as a substrate, generating hydrogen peroxide which flows through a timing barrier 17 into the measurement zone 16 on the device. The length of the color bar developed in the measurement zone is proportional to the concentration of the LDL in the whole blood sample.

More specifically, during the first ten minutes, the reactions in zone 13 are as follows:

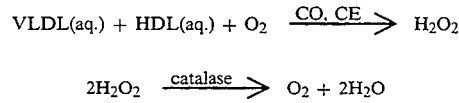

During this stage, the $LDL_{ppt}$ is not oxidized by air, despite the presence of CO and CE.

During the next five minutes, the reactions in layer 13 are as follows:

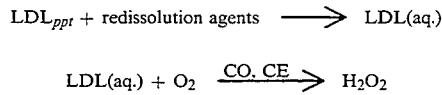

The hydroxylamine inhibits catalase-mediated enzymolysis of the $H_2O_2$.

The device of the present invention can be used with a different enzyme system, as shown in FIG. 2. In FIG. 2, whole blood is introduced into the device 10 at 20, the top of layer 11. Red blood cells are trapped in zone 11, and plasma enters zone 13. A particle enhanced LDL precipitation reagent 38 in zone 13 causes LDL to precipitate in large clusters 22 in less than 60 seconds. In addition, zone 13 is buffered to about pH 9, and contains cholesterol esterase, cholesterol oxidase, cholesterol dehydrogenase (CDH), redissolution agents, NAD, surfactants and cation exchange resins. HDL in the plasma reacts with cholesterol esterase, cholesterol dehydrogenase and NAPD to produce NAPDH, while the LDL precipitate remainsunaffected. The pH in zone 13 drops with time because of the cation exchange resins which was placed inside this zone. Additionally, as the pH falls from 9.0 to 7.0, the cholesterol dehydrogenase becomes inactivated, while the cholesterol oxidase and protease become activated. The LDL precipitate is then dissolved by the protease, and cholesterol esterase and cholesterol oxidase react with LDL to generate hydrogen peroxide. The hydrogen peroxide so generated flows through the timing barrier 17 into the measurement zone 16. The length of the color bar developed in the measurement zone is proportional to the concentration of the LDL in the whole blood sample.

Of course, it will be appreciated that the device specifically disclosed herein for use in assaying for low density lipoprotein are not the only devices in which the system for assaying for low density lipoprotein can be used. The system of the present invention can be used with any suitable device which provides a means for forming and trapping clusters of LDL which can be separated from HDL for analysis.

EXAMPLE 1

A specific precipitation reagent for an undiluted plasma sample can be optimized by varying the concentration of magnesium chloride in the presence of 10 gram/L dextran sulfate (MW 50,000). As shown in Table 1, at 75 mM magnesium chloride concentration, only LDL precipitated out of the plasma, while HDL and VLDL remained in the plasma. Table 1 shows the concentration of cholesterol in plasma after precipitation and slow-speed centrifugation.

|      | 500 mM | 250 mM | 125 mM | 75 mM | 50 mM | 25 mM | 10 mM |
|------|--------|--------|--------|-------|-------|-------|-------|
| VLDL | 1.0    | 1.0    | 3.5    | 43.5  | 43.0  | 43.0  | 42.5  |
| LDL  | 1.0    | 0      | 1.0    | 0.5   | 3.0   | 148.0 | 153.5 |
| HDL  | 40.0   | 40.1   | 38.9   | 40.4  | 40.0  | 41.0  | 40.3  |

It can be discerned from the above that the optimum amount of magnesium chloride for forming a precipitate of LDL ranges from about 75 mM to about 500 mM. In this case, the LDL is precipitated preferentially from the VLDL and HDL. However, as shown in Example 2, the LDL precipitates formed are not stable in the presence of cholesterol enzymes such as cholesterol esterase and cholesterol oxidase, which enzymes are used to consume the HDL and VLDL from the sample so that these latter lipoproteins do not interfere with the LDL assay.

EXAMPLE 2

Samples of 500 μL plasma with known assayed values of VLDL, HDL and LDL were treated with an LDL precipitating reagent with and without nucleating agents (40 mg porous iron oxide particles/mL solution) for one minute. The nucleating agent of choice was porous iron oxide, with average diameters ranging from 1 to 10 microns. After the precipitates were formed, an enzyme reagent containing 4 mg of sodium cholate and 30 units of cholesterol esterase was added to each sample. After three minutes of incubation, the precipitates were spun down at 3000 RPM and the supernatants were assayed for cholesterol values. The data in Table 2 show that the LDL precipitate formed with the nuclei remained insoluble in the presence of surfactant and cholesterol esterase, unlike clusters formed in Example 1 in the absence of nucleating particles.

|               | HDL + VLDL | LDL + ENZYME | % DISSOLUTION |
|---------------|------------|--------------|---------------|
| LDL PPT.      | 65         | 110          | 100           |
| LDL PPT. W/ NUCLEI | 64    | 7            | 6             |

Not all small particles tested exhibited similar effects for precipitating LDL. Particles such as silica and powdered glass worked well to enhance the size of the precipitates, but they did not speed up the formation of the precipitates significantly. By using particles of porous iron oxide, the preferred nucleating agent, large precipitates of LDL clusters form in less than 60 seconds in samples of plasma. Other particles were tried as nucleating agents, as described in the above example, with the results shown below:

| CHARACTERISTICS OF NUCLEATING AGENT PARTICLES FOR LIPOPROTEIN PRECIPITATION ENHANCEMENT | | | | |
|---|---|---|---|---|
| Type of Particle | Size | Pellet formation | Ease of redissolution | Completeness of precipitation |
| Iron oxides | 0.6–10 μm | good solid pellet | Yes | 95–100% |
| Iron powder | 100 μm | solid pellet | No | 45–80% |
| Chromium dioxide | 0.5–20 μm | solid pellet | Yes | 80–85% |
| Titanium dioxide | irregular | solid pellet | No | 70–80% |
| Silica gel | 4–20 μm | poor pellet | No | 50–94%* |
| Sand | 200–400 μm | poor pellet | No | 50–96%* |
| Activated charcoal | 38–150 μm | good pellet | No | 75–85% |
| Cellulose | 6 μm | poor pellet | No | 60–80% |
| Kaolin | 0.1–4 μm | poor pellet | No | 75–79% |

*Most runs were 50%–60%.

EXAMPLE 3

In order to determine the presence and/or amount of LDL in a sample, the clusters formed must be destroyed and the LDL must be redissolved in the solution. Redissolution agents are used to redissolve the LDL. In this example, the LDL precipitate obtained in Example 2 was redissolved using redissolution agents. The most effective formulation for redissolving the LDL precipitate comprised a mixture of EDTA and sodium chloride.

In one embodiment, for about 400 μL of samples, the final amount of sodium chloride in the sample is from about 2.5–6.5%, and the amount of EDTA is from about 0.05–0.12%. As shown in Table 3, LDL precipitates formed by the nucleated precipitating agents dissolved in less than 30 seconds after the redissolution agents were introduced, and the recovery of lipoprotein in the solution was close to 100%. Preferably, recovery is at least 90%, more preferably at least 95%.

| LDL IN SAMPLE | 197 mg/dL | |
|---|---|---|
| LDL in supernatant after ppt. | 2 mg/dL | |
| LDL after re-dissolution of precipitates | 186 mg/dL | (95% recovery) |

The foregoing description of the specific embodiments will so fully reveal the general nature of the invention that others can, by applying current knowledge, readily modify and/or adapt for various applications such specific embodiments without departing from the generic concept. Therefore, such adaptations and modifications are intended to be comprehended within the meaning and range of equivalents of the disclosed embodiments. It is to be understood that the phraseology or terminology herein is for the purpose of description and not of limitation.

FIGURE LEGEND

10 assay device
11 layer for trapping red blood cells
13 LDL precipitation zone
14 zone with sucrose coating
15 Hydroxylamine and LDL redissolution agents
16 measurement zone
17 timing barrier
20 sample initiation area
21 particle enhanced LDL precipitation reagent
22 clusters of LDL
38 LDL precipitation reagent

What is claimed is:

1. A process for direct determination of low density lipoprotein in a fluid sample comprising:
   adding a polyanionic compound, a salt of a divalent metal, and an insoluble nucleating agent to the fluid sample to form clusters of low density lipoprotein;
   adding enzymes to consume high density lipoprotein and very low density lipoprotein selectively from said fluid sample; and
   resolubilizing the low density lipoprotein and determining the amount of low density lipoprotein in the sample.

2. The process according to claim 1 wherein said polyanionic compound is selected from the group consisting of dextran sulfate, heparin, phosphotungstic acid, and polyvinyl sulfate.

3. The process according to claim 1 wherein said divalent metal is selected from the group consisting of group II-A and II-B metals.

4. The process according to claim 3 wherein said divalent metal is selected from the group consisting of calcium, manganese, and magnesium.

5. The process according to claim 1 wherein said nucleating agent is iron oxide.

6. The process according to claim 5 wherein said iron oxide is porous.

7. The process according to claim 1 wherein said nucleating agent is coated with the polyanionic compound.

8. The process according to claim 1 wherein said low density lipoprotein is determined enzymatically.

9. The process according to claim 1 wherein said resolubilizing is effected by adding a redissolution agent which changes the ionic strength of the sample selected from the group consisting of a mixture of EDTA and sodium chloride, protease, and magnesium chloride.

* * * * *